US011393571B2

(12) United States Patent
Crume (10) Patent No.: US 11,393,571 B2
(45) Date of Patent: Jul. 19, 2022

(54) FUNCTIONAL GARMENTS AND METHODS THEREOF

(71) Applicant: Ryan K. Crume, Newport Beach, CA (US)

(72) Inventor: Ryan K. Crume, Newport Beach, CA (US)

(*) Notice: Subject to any disclaimer, the term of this patent is extended or adjusted under 35 U.S.C. 154(b) by 0 days.

(21) Appl. No.: 15/230,298

(22) Filed: Aug. 5, 2016

(65) Prior Publication Data

US 2017/0036054 A1 Feb. 9, 2017

Related U.S. Application Data

(60) Provisional application No. 62/202,806, filed on Aug. 8, 2015.

(51) Int. Cl.
*A63B 21/04* (2006.01)
*G16H 20/30* (2018.01)
(Continued)

(52) U.S. Cl.
CPC ......... *G16H 20/30* (2018.01); *A41D 13/0015* (2013.01); *A41D 31/185* (2019.02); *A61B 5/02438* (2013.01); *A61B 5/6802* (2013.01); *A63B 21/0552* (2013.01); *A63B 21/4025* (2015.10); *B32B 1/00* (2013.01); *B32B 3/02* (2013.01); *B32B 5/06* (2013.01); *B32B 5/26* (2013.01); *B32B 7/022* (2019.01); *A63B 21/4005* (2015.10); *A63B 21/4007* (2015.10); *A63B 21/4009* (2015.10); *A63B 21/4011* (2015.10); *A63B 21/4017* (2015.10); *A63B 2071/0625* (2013.01); *A63B 2209/10* (2013.01); *A63B 2220/12* (2013.01);
(Continued)

(58) Field of Classification Search
CPC ................ A61N 1/0484; A61B 5/6805; A41D 2400/38; A41D 13/00; A41D 13/0012; A41D 13/0002; A41C 1/00; A41C 1/08
See application file for complete search history.

(56) References Cited

U.S. PATENT DOCUMENTS

| | | | |
|---|---|---|---|
| 4,065,814 A | 1/1978 | Fox | |
| 4,729,377 A * | 3/1988 | Granek | A61B 5/04085 600/382 |

(Continued)

*Primary Examiner* — Alyssa M Alter
(74) *Attorney, Agent, or Firm* — Rutan & Tucker LLP; Hani Z. Sayed (57) ABSTRACT

Provided herein in some embodiments is a resistance-training system including an upper-body garment having a first section of a single-layered construction and a second section of a multi-layered construction. The single-layered construction can include a first fabric layer. The multi-layered construction can include the first fabric layer, a second fabric layer, and a resistance-providing layer in-between the first fabric layer and the second fabric layer. The resistance-training system also includes a lower-body garment having the multi-layered construction, optionally with a different resistance-providing layer than the upper-body garment. The resistance-providing layer of the upper-body garment and the lower-body garment can be configured to provide resistance to one or more user movements for a user donning the resistance-training system.

14 Claims, 8 Drawing Sheets

(51) Int. Cl.
*A41D 13/00* (2006.01)
*A61B 5/024* (2006.01)
*A61B 5/00* (2006.01)
*A63B 21/00* (2006.01)
*B32B 3/02* (2006.01)
*A63B 21/055* (2006.01)
*B32B 5/26* (2006.01)
*B32B 1/00* (2006.01)
*B32B 5/06* (2006.01)
*A41D 31/18* (2019.01)
*B32B 7/022* (2019.01)
*A63B 71/06* (2006.01)

(52) U.S. Cl.
CPC ....... *A63B 2220/17* (2013.01); *A63B 2220/20* (2013.01); *A63B 2220/30* (2013.01); *A63B 2220/62* (2013.01); *A63B 2220/73* (2013.01); *A63B 2225/50* (2013.01); *A63B 2230/06* (2013.01); *A63B 2230/75* (2013.01); *B32B 2307/50* (2013.01); *B32B 2307/51* (2013.01); *B32B 2437/00* (2013.01); *B32B 2571/00* (2013.01)

(56) References Cited

U.S. PATENT DOCUMENTS

| | | | |
|---|---|---|---|
| 5,659,898 A * | 8/1997 | Bell, Jr. | A41D 13/0015 2/115 |
| 5,778,452 A | 7/1998 | Dicker et al. | |
| 6,231,488 B1 | 5/2001 | Dicker et al. | |
| 8,795,138 B1 | 8/2014 | Yeh et al. | |
| 2007/0032981 A1* | 2/2007 | Merkel | A61B 5/6831 702/160 |
| 2011/0209264 A1* | 9/2011 | Williams | A41D 13/0015 2/69 |

* cited by examiner

FIG. 1

FIG. 2
FRONT

FIG. 3
BACK

FIG. 6
FRONT

FIG. 7
BACK

FIG. 8
FRONT

FIG. 9
BACK

FUNCTIONAL GARMENTS AND METHODS THEREOF

CROSS-REFERENCE

This application claims the benefit of U.S. Provisional Patent Application No. 62/202,806, titled "Combining Resistance Bands And Fitness Tracking Technology With Clothing To Create Functional Garments," filed Aug. 7, 2015, which application is incorporated herein by reference in its entirety.

BACKGROUND

As our lives become increasingly busy, it becomes increasingly difficult to establish and maintain a proper physical fitness or physical therapy regimen. Changes in career, health, family dynamic, age, social patterns in addition to many other circumstances can all be contributing factors that distract from an active lifestyle. Further, the inability of someone to track or edit one's biometric fitness data promotes a sedentary lifestyle by preventing the user from seeing the benefits of their efforts. As a consequence, the lack of regular participation in moderate physical activity can have detrimental effects on the human body. Not only are risk factors for serious health conditions increased, but cognitive function is also negatively affected. Provided herein are systems and methods that address the foregoing.

SUMMARY

Provided herein in some embodiments is a resistance-training system including an upper-body garment having a first section of a single-layered construction and a second section of a multi-layered construction. The single-layered construction can include a first fabric layer. The multi-layered construction can include the first fabric layer, a second fabric layer, and a resistance-providing layer in-between the first fabric layer and the second fabric layer. The resistance-training system also includes a lower-body garment having the multi-layered construction, optionally with a different resistance-providing layer than the upper-body garment. The resistance-providing layer of the upper-body garment and the lower-body garment can be configured to provide resistance to one or more user movements for a user donning the resistance-training system.

DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

As used herein, "fabric" includes materials made of interlacing natural fibers, synthetic fibers, or natural and synthetic fibers generally considered suitable for use in garments.

As used herein, "anchoring" or "attaching" includes without limitation any one or more of sewing, gluing, and heat-bonding to accomplish the anchoring or attaching.

Unless defined otherwise, all technical and scientific terms used herein have the same meaning as commonly understood those of ordinary skill in the art.

As our lives become increasingly busy, it becomes increasingly difficult to establish and maintain a proper physical fitness or physical therapy regimen. Changes in career, health, family dynamic, age, social patterns in addition to many other circumstances can all be contributing factors that distract from an active lifestyle. Further, the inability of someone to track or edit one's biometric fitness data promotes a sedentary lifestyle by preventing the user from seeing the benefits of their efforts. As a consequence, the lack of regular participation in moderate physical activity can have detrimental effects on the human body. Not only are risk factors for serious health conditions increased, but cognitive function is also negatively affected. Provided herein are systems and methods that address the foregoing.

Provided herein in some embodiments is a resistance-training system including an upper-body garment having a first section of a single-layered construction and a second section of a multi-layered construction. The single-layered construction can include a first fabric layer. The multi-layered construction can include the first fabric layer, a second fabric layer, and a resistance-providing layer in-between the first fabric layer and the second fabric layer. The resistance-training system also includes a lower-body garment having the multi-layered construction, optionally with a different resistance-providing layer than the upper-body garment. The resistance-providing layer of the upper-body garment and the lower-body garment can be configured to provide resistance to one or more user movements for a user donning the resistance-training system.

Figures 1, 2:
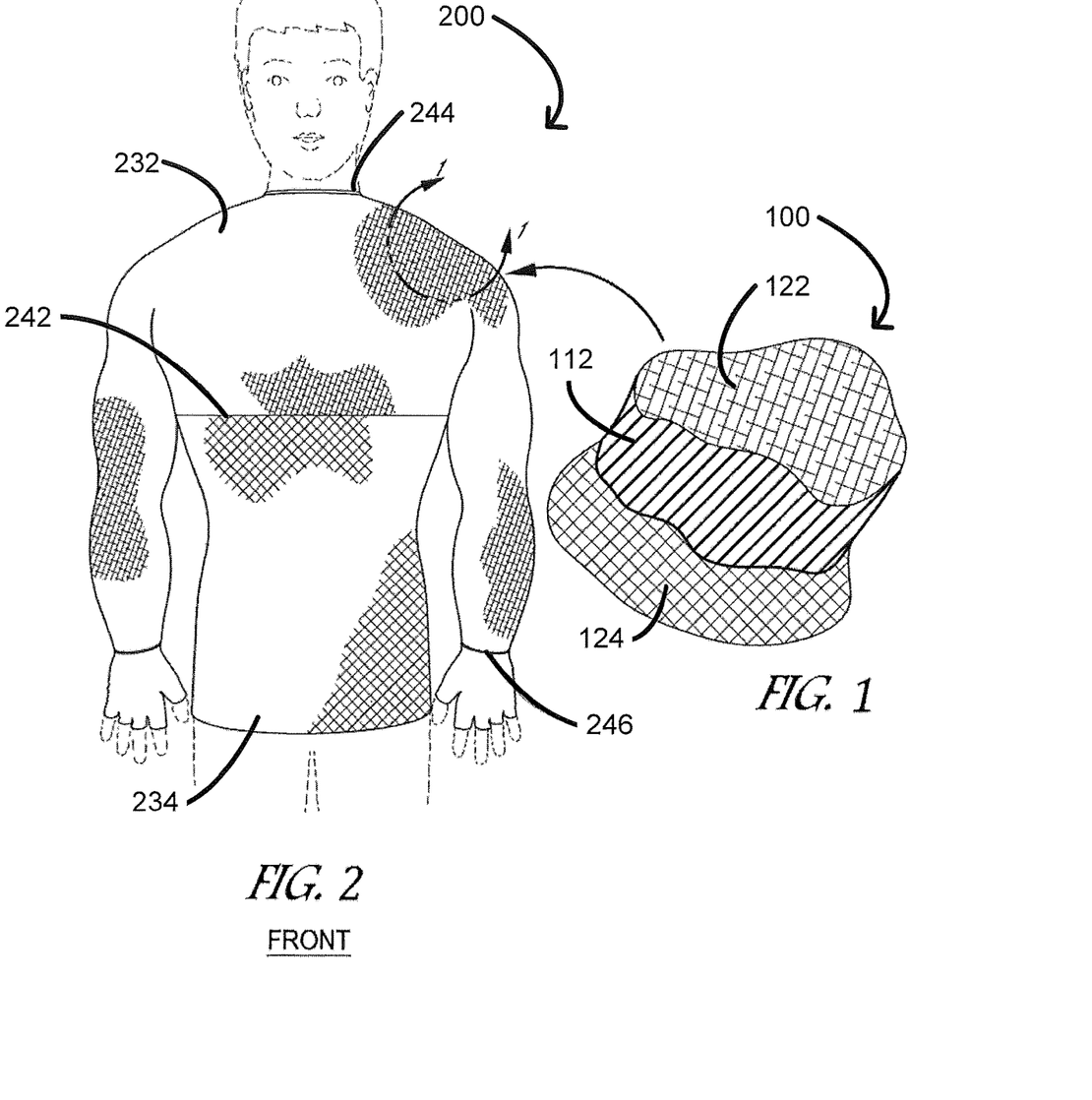
FIG. 1 shows an enlarged cross-section of a garment having a multi-layered construction in accordance with some embodiments.
FIG. 2 shows a front view of an upper-body garment in accordance with some embodiments.

FIG. 1 shows an enlarged cross-section of a garment having a multi-layered construction 100 in accordance with some embodiments.

The cross-section of FIG. 1 shows the multi-layered construction 100 of the garment or sections of the garment. The multi-layered construction can include one or more fabric layers together with one or more resistance-providing layers. In some embodiments, a resistance-providing layer includes an elastic material 112 in-between a first layer of a first fabric 122 and a second layer of a second fabric 124, wherein the first fabric and the second fabric are the same fabric or different fabrics.

The first fabric 122 and the second fabric 124 can be the same fabric or different fabrics in accordance with the benefits desired. For example, the first fabric 122 and the second fabric 124 can be the same fabric, the benefits of which include less complex manufacturing and overall cost savings. For example, the first fabric 122 and the second fabric 124 can be different fabrics, the benefits of which include options for inner-facing or skin-facing fabrics (e.g., a soft skin-facing fabric) and outer-facing fabrics (e.g., a weatherproof outer-facing fabric).

The elastic material 112 can be free to expand or contract in-between the layers of fabric in the garment. The elastic material 112 can also form an inner core of the garment, wherein the same elastic material forms the inner core or a variety of elastic materials form the inner core, each elastic material having a different degree of elasticity (e.g., modulus of elasticity) to create a different degree of resistance in the garment. The elastic material 112 can be an elastic fabric with interlacing elastomeric fibers or an elastic sheet (no interlacing fibers) of an elastomeric material. Additionally or alternatively, the elastic material 112 can include one or more elastic bands or tubes stitched in-between the layers of fabric in the garment, wherein each of the one or more elastic bands is positioned in the garment to oppose a natural motion of a one or more muscles.

Gradations of resistance can be used to tailor the garment to a specific industry need. Lightweight resistance is well suited for physical therapy or rehabilitation purposes while heavyweight resistance is better suited for strength-training or sports-training applications.

FIG. 2 shows a front view of an upper-body garment 200 in accordance with some embodiments.

The upper-body garment 200 can be configured as a long-sleeved shirt. As provided in reference to FIG. 1, a garment such as the upper-body garment 200 or sections thereof can have the multi-layered construction 100. For example, as shown in FIG. 2, a top section 232 of the upper-body garment 200 can include the multi-layered construction 100 while a bottom section 234 of the upper-body garment can include a different construction such as a single-layered construction. The single-layered construction can include the first fabric 122, the second fabric 124, or a different fabric than any of the fabrics in the top section 232. Material transition line 242 separates the top section 232 and the lower section 234 of the upper-body garment 200 having the different constructions.

The layers of the first fabric 122, the second fabric 124, and the elastic material 112 can be anchored to one another in opposing hems including at a collar 244, a material transition line 246, and the material transition line 242 of the upper-body garment 200, wherein the hem at the collar 244 opposes the hems at the material transition line 246 and the material transition line 242. The layer of the elastic material 112 within, for example, the left and right arms, can be of a shorter length than the layers of the first fabric 122 and the second fabric 124. Anchoring the elastic material 112 between opposing hems with the shorter length provides a hem proximity-based basal resistance to one or more user movements for a user donning the upper-body garment 200. It should be appreciated that in addition to hem proximity and the shorter length of the layer of the elastic material 112, the basal resistance can also be dependent upon the modulus of elasticity of the elastic material 112. The elastic material 112 is configured to freely stretch in-between the layers of the first fabric 122 and the second fabric 124.

The material transition line 246 marks a point on the upper-body garment 200 at which the hem on the left sleeve is attached to a glove or a hand loop enabling the user to engage and stretch the elastic material 112 to the length of his/her left arm. Likewise, the hem on the right sleeve is attached to a glove or a hand loop enabling the user to engage and stretch the elastic material 112 to the length of his/her right arm. A glove 252 is shown in FIG. 3 as an example of the foregoing.

Figure 3:
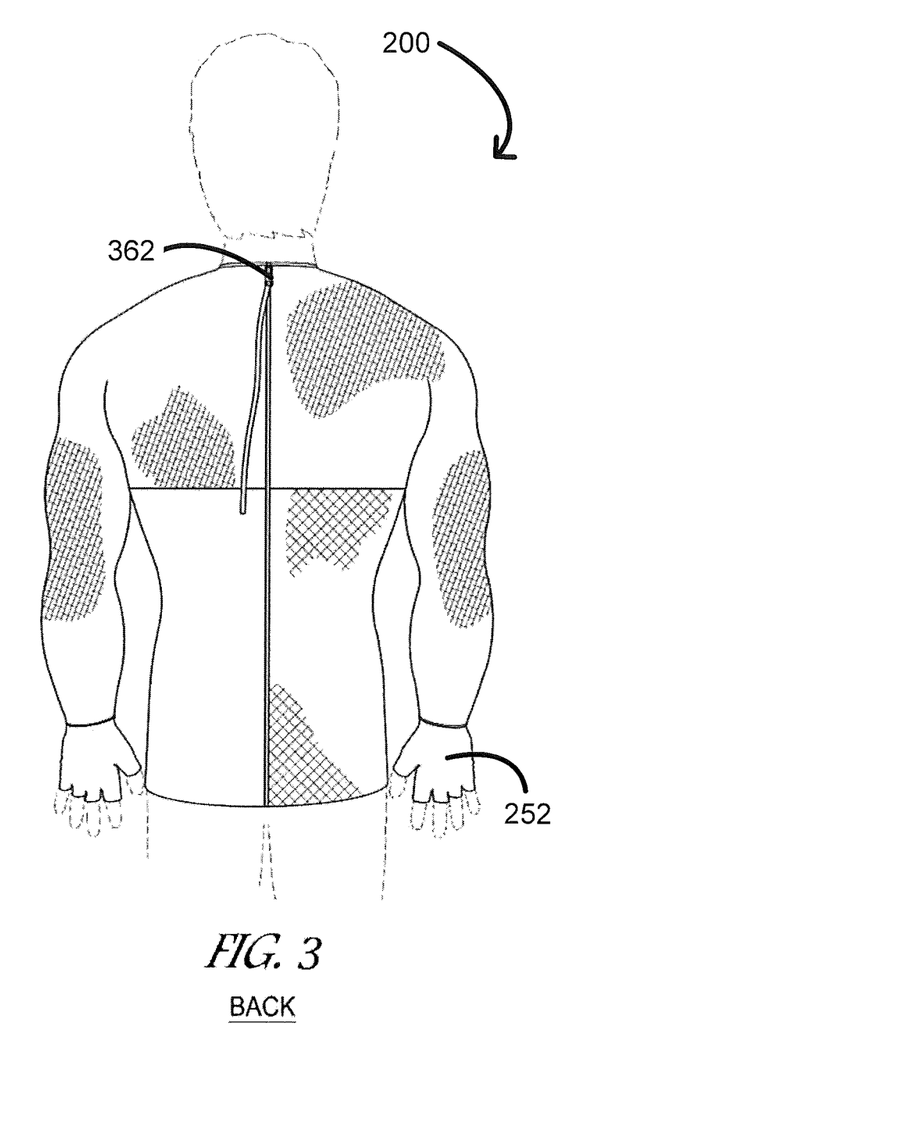
FIG. 3 shows a back view of the upper-body garment in accordance with some embodiments.

FIG. 3 shows a back view of the upper-body garment 200 in accordance with some embodiments.

A zipper 362 can be incorporated into the upper-body garment 200 in order to facilitate easy transition into and out of the upper-body garment 200. It should be appreciated that the location of the zipper 362 can vary from the location illustrated in FIG. 3. It should also be appreciated that fasteners other than zippers including buttons, snaps, laces, Velcro®, and the like can be used in the same location as the zipper 362.

Figure 4:
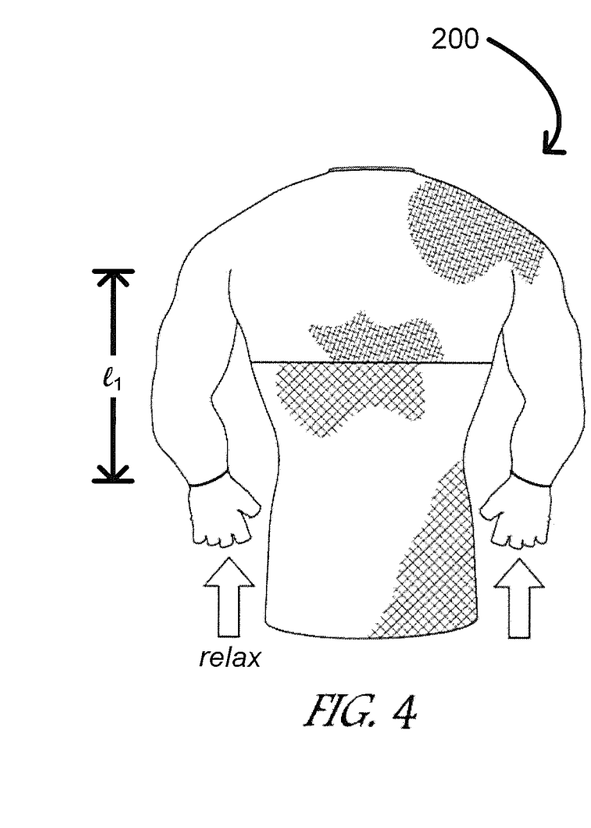
FIG. 4 shows a front view of the upper-body garment when the garment is not being worn and resistance is not being applied in accordance with some embodiments.

FIG. 4 shows a front view of the upper-body garment 200 when the upper-body garment 200 is not being worn and resistance is not being applied in accordance with some embodiments.

As shown in FIG. 4, when the upper-body garment 200 is not being worn by a user, the sleeves are relaxed and in a contracted, natural resting state. Indeed, the sleeves exhibit a length $l_1$ corresponding to the shorter length of the layer of the elastic material 112 in-between the longer length of the layers of the first fabric 122 and the second fabric 124. Without the user's arms in the sleeves of the upper-body garment 200, the sleeves are not stretched; therefore, there is no resistance created.

Figure 5:
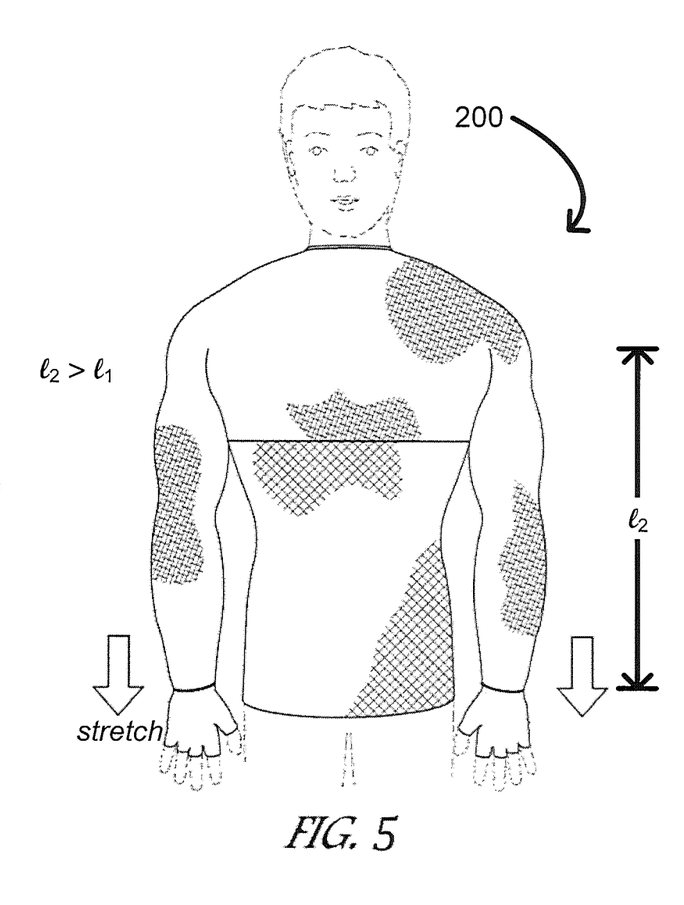
FIG. 5 shows a front view of the upper-body garment when the garment is being worn and resistance is being applied in accordance with some embodiments.

FIG. 5 shows a front view of the upper-body garment 200 when the garment is being worn and resistance is being applied in accordance with some embodiments.

As shown in FIG. 5, when the user inserts his or her arms into the upper-body garment 200, the sleeves of the upper-body garment 200 are stretched and resistance is established. Indeed, the sleeves exhibit a length $l_2$ corresponding to the longer length of the layers of the first fabric 122 and the second fabric 124. The layer of elastic material 112 is stretched from the contracted, natural resting state with a length $l_1$ to the length $l_2$, thereby creating the resistance against the user.

Figures 6, 7:
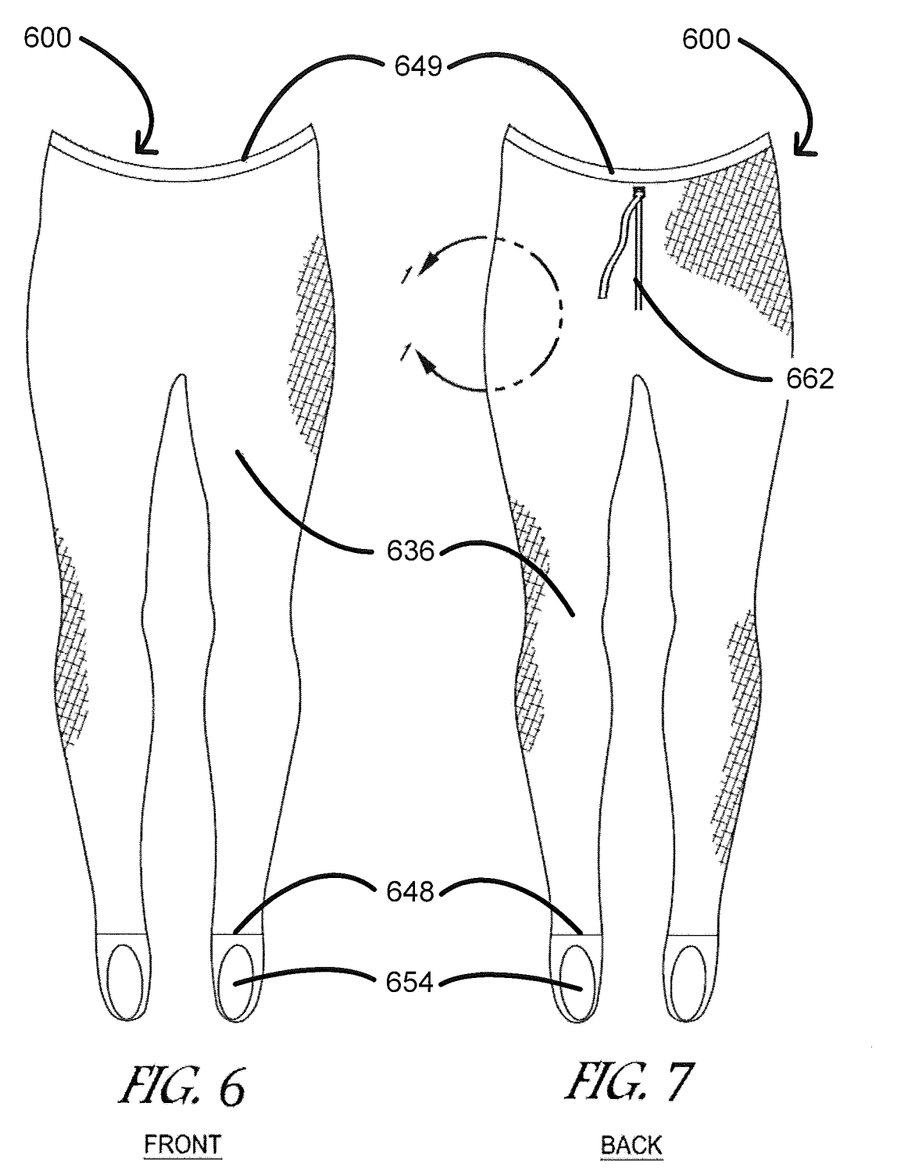
FIG. 6 shows a front view of a lower-body garment without an upper-body garment in accordance with some embodiments.
FIG. 7 shows a back view of the lower-body garment without an upper-body garment in accordance with some embodiments.

FIG. 6 shows a front view of a lower-body garment 600 without an upper-body garment in accordance with some embodiments.

The lower-body garment 600 can be configured as long pants or leggings. As provided in reference to FIG. 1, a garment such as the lower-body garment 600 or sections thereof can have the multi-layered construction 100. For example, as shown in FIG. 6, the lower-body garment 600 can include the multi-layered construction 100 between a material transition line 648 and a waist band 649.

The layers of the first fabric 122, the second fabric 124, and the elastic material 112 can be anchored to one another in opposing hems including at the material transition line 648 and the waist band 649 of the lower-body garment 600, wherein the hem at the material transition line 648 opposes the hem at the waist band 649. The layer of the elastic material 112 within, for example, the left and right pantlegs, can be of a shorter length than the layers of the first fabric 122 and the second fabric 124. Anchoring the elastic material 112 between opposing hems with the shorter length provides a hem proximity-based basal resistance to one or more user movements for a user donning the lower-body garment 600. It should be appreciated that in addition to hem proximity and the shorter length of the layer of the elastic material 112, the basal resistance can also be dependent upon the modulus of elasticity of the elastic material 112. As with the upper-body garment 200, the elastic material 112 in the lower-body garment 600 is configured to freely stretch in-between the layers of the first fabric 122 and the second fabric 124. To accommodate for greater leg strength over aim strength, the elastic material 112 of the lower-body garment 600 can be different than the elastic material 112 of the upper-body garment 200. For example, the elastic material 112 of the lower-body garment 600 can have a higher modulus of elasticity.

The material transition line 648 marks a point on the lower-body garment 600 at which the hem on the left pantleg is attached to a heel strap or stirrup 654 enabling the user to engage and stretch the elastic material 112 to the length of his or her left leg. Likewise, the hem on the right pantleg is attached to a heel strap or stirrup 654 enabling the user to engage and stretch the elastic material 112 to the length of his or her right leg.

The waist band 649 can be configured to be sufficiently tight in order to overcome the downforce created by the resistance of the lower-body garment 600 when worn by the user. Additionally or alternatively, the lower-body garment 600 can be configured with suspenders that overcome the downforce created by the resistance of the lower-body garment 600 when worn by the user.

FIG. 7 shows a back view of the lower-body garment 600 without an upper-body garment in accordance with some embodiments.

A zipper 662 can be incorporated into the lower-body garment 600 in order to facilitate easy transition into and out of the lower-body garment 600. It should be appreciated that the location of the zipper 662 can vary from the location illustrated in FIG. 7. It should also be appreciated that fasteners other than zippers including buttons, snaps, laces, Velcro®, and the like can be used in the same location as the zipper 662.

Figure 8:
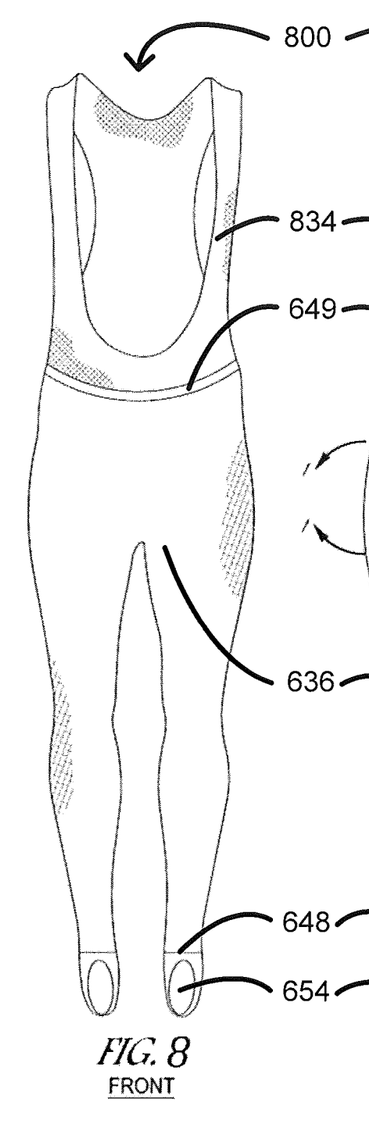
FIG. 8 shows a back view of a garment in accordance with some embodiments.
Figure 9:
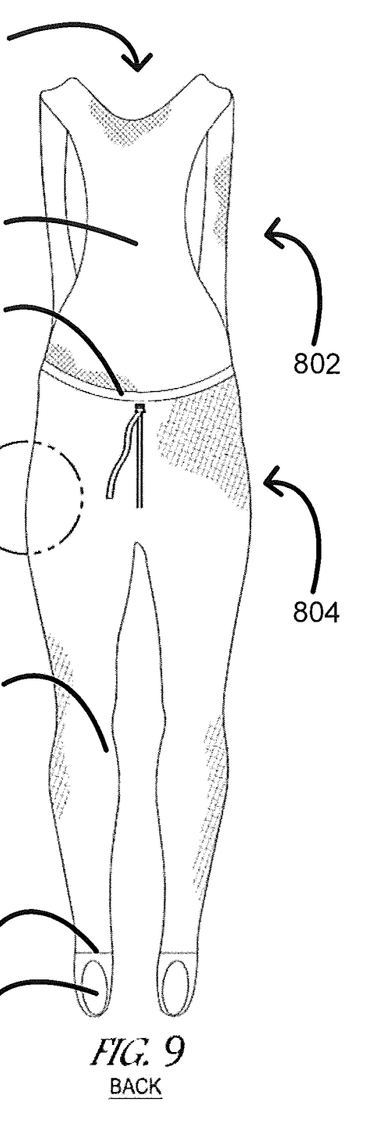
FIG. 9 shows a front view of a garment in accordance with some embodiments.

FIG. 8 shows a back view of a garment 800 in accordance with some embodiments. FIG. 9 shows a front view of the garment 800 in accordance with some embodiments.

As shown in FIGS. 8 and 9, the garment 800 can have an upper-body portion 802 and a lower-body portion 804. While the upper-body portion 802 can be the upper-body garment 200 provided herein, an alternative to the upper-body garment 200 is a bib 834 as shown. Like the bottom section 234 of the upper-body garment 200, the bib 834 can have a single-layered construction. The single-layered construction can include the first fabric 122, the second fabric 124, or a different fabric than any of the fabrics in the top section 232 of the upper-body garment 200. The lower-body portion 804 can be the lower-body garment 600 provided herein.

Alternatively, the garment 800 can be configured as a single unit or unitary garment incorporating features of the bib 834 in the upper-body portion 802 of the unitary garment and features of the lower-body garment 600 in the lower-body portion 804 of the unitary garment. In some embodiments, for example, the unitary garment includes substantially all the features of the bib 834 and the lower-body garment 600 provided herein. In such embodiments, the bib 834 can be anchored to the lower-body garment 600 in the hem at the waist band 649 of the lower-body garment 600. Furthermore, in such embodiments, the unitary garment can include a zipper in a back of the unitary garment, wherein the zipper extends from an area just above a waist (e.g., small of back) of the unitary garment to about a seat of the unitary garment. It should also be appreciated that fasteners other than zippers including buttons, snaps, laces, Velcro®, and the like can be used in the same location as the foregoing zipper.

Whether the garment 800 is configured as a separable garment (e.g., the bib 834 and the lower-body garment 600 are separable) or as a unitary garment, the bib 834 can serve to support a downforce created by the resistance of the garment when worn by the user.

Figure 10:
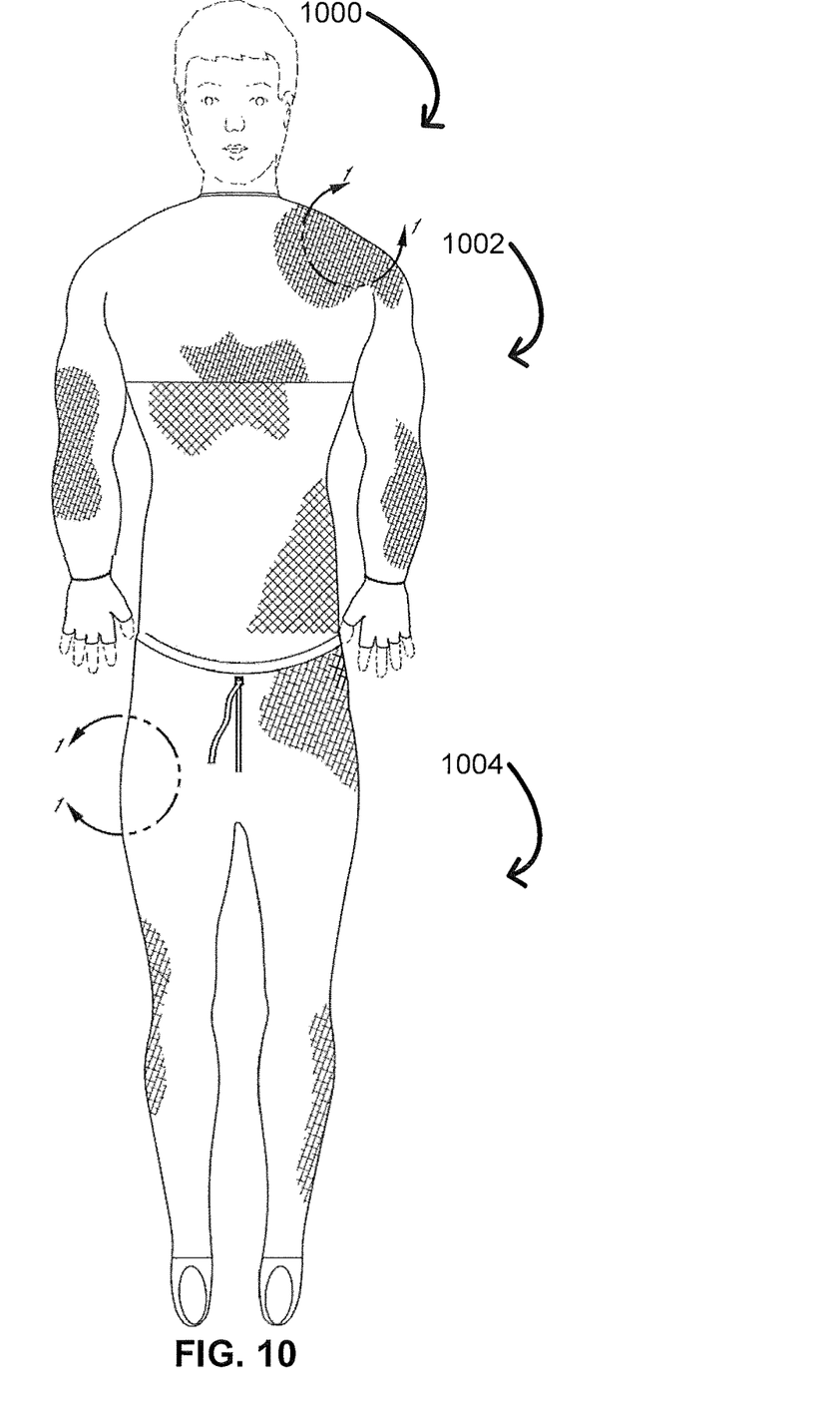
FIG. 10 shows a front view of a garment in accordance with some embodiments.

FIG. 10 shows a front view of a garment 800 in accordance with some embodiments.

As shown in FIG. 10, the garment 1000 can have an upper-body portion 1002 and a lower-body portion 1004. The upper-body portion 1002 can be the upper-body garment 200 provided herein, and the lower-body portion 1004 can be the lower-body garment 600 provided herein. Alternatively, the garment 1000 can be configured as a single unit or unitary garment incorporating features of the upper-body garment 200 in the upper-body portion 1002 of the unitary garment and features of the lower-body garment 600 in the lower-body portion 1004 of the unitary garment. In some embodiments, for example, the unitary garment includes substantially all the features of the upper-body garment 200 and the lower-body garment 600 provided herein. In such embodiments, the bottom section 234 of the upper-body garment 200 can be anchored to the lower-body garment 600 in the hem at the waist band 649 of the lower-body garment 600. Furthermore, in such embodiments, the unitary garment can include a zipper in a back of the unitary garment, wherein the zipper extends from a collar of the unitary garment to about a waist (or seat) of the unitary garment. It should also be appreciated that fasteners other than zippers including buttons, snaps, laces, Velcro®, and the like can be used in the same location as the foregoing zipper.

Figure 11:
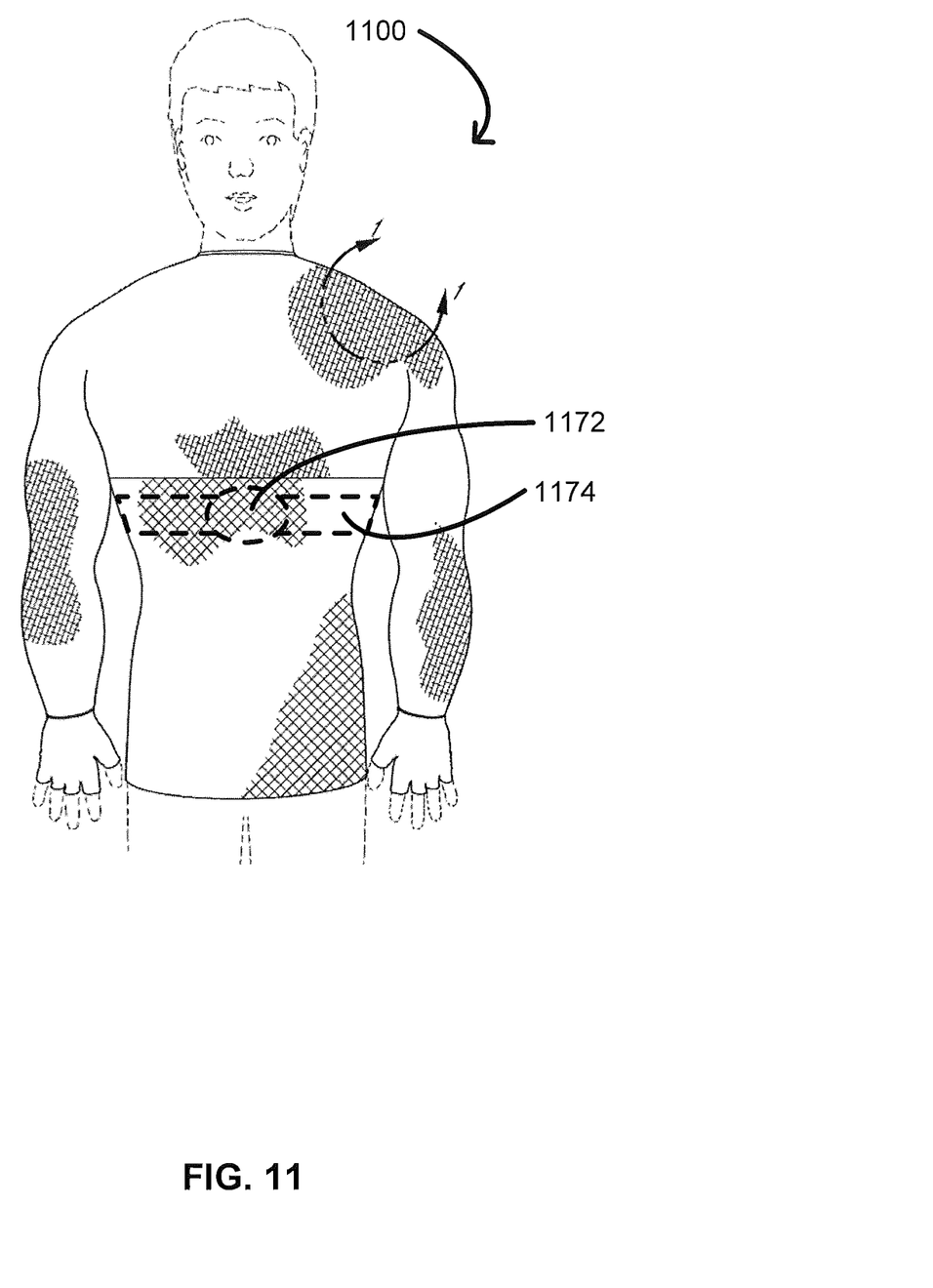
FIG. 11 shows a front view of an upper-body garment with an incorporated fitness-tracking device in accordance with some embodiments.

FIG. 11 shows a front view of an upper-body garment 1100 with an incorporated fitness-tracking device in accordance with some embodiments.

One or more fitness-tracking devices or other wearable electronic devices ("garment devices") can be removeably incorporated into one or both garments of the upper-body garment and the lower-body garment. Any one or more of the garment devices can be configured to collect fitness-related data selected from heart rate, steps taken, distance traveled, elevation, pace, calories burned, active minutes, stationary time, and the like. With such garment devices, a user can identify, track, record, extract, and/or edit various performance statistics. Any one or more of the garment devices can be additionally or alternatively configured to provide functionality such as music playback, music playback control, GPS, and mobile phone integration.

As shown in FIG. 11, for example, a heart rate monitor 1172 with an optional securing strap 1174 can be removeably incorporated in the upper-body garment 1100. The heart rate monitor 1172 or any other garment device can be removeably incorporated into a garment by placing the garment device into a pocket or pouch designed for the garment device. It should be understood that the garment can be designed to accommodate garment devices in other ways as well. For example, the garment can be designed with clips or snaps for clipping or snapping garment devices onto the garment. Whether by a pocket, a pouch, a clip, a snap, or the like, the garment device can be removeably incorporated in a suitable location for collecting fitness-related data. For example, the heart rate monitor shown in FIG. 11 is in a suitable location for collecting heart rate data.

Removeably incorporating a garment device allows for removing the garment device from a garment for wired charging or data transfer if the garment device is not configured for wireless charging or data transmission. In addition, removeably incorporating a garment device allows it to be swapped out for any other garment device the user desires.

Figure 12:
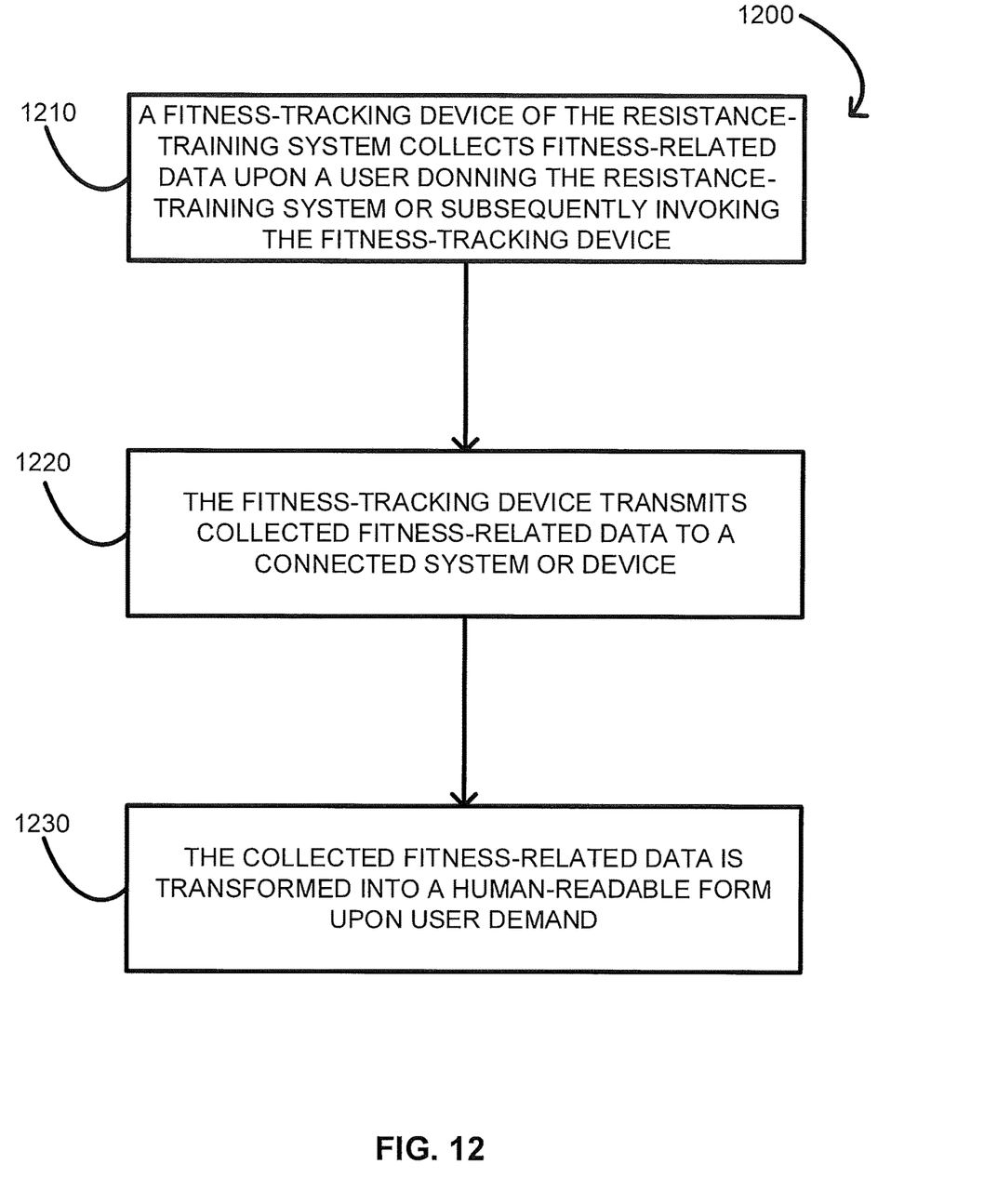
FIG. 12 shows a process by which fitness-related data is extracted in accordance with some embodiments.

FIG. 12 shows a process 1200 by which fitness-related data is extracted in accordance with some embodiments.

As shown, the process 1200 can include a step 1210 whereby a fitness-tracking device of the resistance-training system collects fitness-related data upon a user donning the resistance-training system or subsequently invoking the fitness-tracking device. The resistance-training system can be any garment provided herein. If the fitness-tracking device is not configured to wake from a low-energy sleep mode upon sensing physical activity on behalf of the user donning the garment, the user can manually invoke the fitness-tracking device.

The process 1200 can further include a step 1220 whereby the fitness-tracking device transmits collected fitness-related data to a connected system or device. If configured with a wireless interface, the fitness-tracking device can wirelessly connect to the system (e.g., personal computer, server computer, etc.) or device (e.g., smart watch, smart phone, personal digital assistant, etc.) and transmit the collected fitness-related data. Alternatively, the fitness-tracking device can physically connect to the system or device with a data transmission cable. With a wireless connection, transmission of the collected fitness-related data can occur periodically during the physical activity of the user or once the user completes his or her physical activity. With a wired connection, transmission of the collected fitness-related data can occur once the user completes his or her physical activity.

The process can include a step 1230 whereby the collected fitness-related data is transformed into a human readable form upon user demand. If the collected fitness-related data is transmitted to a system or device with a local fitness-tracking module, the local fitness-tracking module can transform the collected fitness-related data into a human-readable form such as charts, graphs, or the like when the user interacts with the local fitness-tracking module through a related user interface (e.g., graphical user interface for a fitness-tracking application). If the collected fitness-related data is transmitted to a system or device with a cloud-based fitness-tracking module, the cloud-based fitness-tracking module can transform the collected fitness-related data in the human-readable form when the user interacts with the cloud-based fitness-tracking module through a related cloud-based user interface (e.g., web browser).

In view of the foregoing, provided herein in some embodiments are systems and methods that incorporate resistance-training elements into clothing to create functional garments. In some embodiments, systems and methods provided herein incorporate wearable technology for biometric fitness tracking. Thus, day-to-day movements and specific activities can be transformed into beneficial, strength-building exercises. In addition, rehabilitation-like activities can be effected by transforming day-to-day activities into therapeutic movements. The resistance-training elements, the wearable technology, or both the resistance-training elements and the wearable technology can be incorporated into lower-body garments, upper-body garments, both lower-body garments and upper-body garments, or single-piece garments.

In one aspect, a method is provided for incorporating elastic workout bands such as resistance bands together with other types of fabric to create a functional upper-body garment. The method includes the creation of a multi-layered upper-body garment including an inner and outer layer of fabric with an embedded layer of resistance band in-between. The embedded layer of resistance band can be designed with a length and a thickness to provide resistance to the user when worn. Users can wear the garment to achieve greater results from a particular workout regimen or incorporate the garment into their rehabilitation schedule to help advance muscle development. When a user inserts his or her arms into the garment, the user's hands can engage a hand grasp, and the shortened length of the elastic inner core of the garment is free to stretch to the length of the inner and outer layers of fabric, thereby creating a path for expansion and contraction of the elastic inner core in-between the inner and outer layers of fabric. The garment can be secured onto the user's torso by a zipper. When worn by the user, the garment can assist in the conversion of day-to-day activities into beneficial movements. By introducing a force to movements that are normally performed without any resistance, the garment effectively transforms normal activities into strength-training and/or therapeutic exercises.

In one aspect, a method is provided for incorporating wearable fitness technology and other data collecting technology into the upper-body garment. The method includes integrating technology for monitoring and recording biometric data related to the activity being performed. Further, the method includes integrating technology for monitoring and recording other performance data related to the activity being performed. Further still, the method can include integrating hardware that allows for the future expansion of developing technologies.

In one aspect, a method is provided for connecting both the upper- and lower-body garments together in order to make a functional resistance suit. The method includes incorporating opposing male and female connections such as buckles, or other securing technology, to the upper- and lower-body garments for the purpose of creating a complete unit when worn together. Users can wear either garment independently or choose to combine the two together as one.

In one aspect, a method is provided for incorporating elastic workout bands such as resistance bands together with other types of fabric to create a functional lower-body garment. The method includes the creation of a multi-layered lower-body garment including an inner and outer layer of fabric with an embedded layer of resistance band in-between. The embedded layer of resistance band can be designed with a length and a thickness to provide a desired resistance to the user when worn. Users can wear the garment to achieve greater results from a particular workout regimen or incorporate the garment into their rehabilitation schedule to help advance muscle development.

In one aspect, a method is provided for incorporating wearable fitness technology and other data collecting technology into the lower-body garment. The method includes integrating technology for monitoring and recording biometric data related to the activity being performed. Further, the method includes integrating technology for monitoring and recording other performance data related to the activity being performed. Further still, the method can include integrating hardware that allows for the future expansion of developing technologies or the incorporation of third-party technologies.

In one aspect, a method is provided for extracting the fitness or performance data collected during the activity being performed. The method includes connection of the upper- or lower-body garments or the wearable fitness technology thereof to a communicatively coupled system or device, either by a wired or wireless interface. The system or device can be any computer or smart device able to communicate with the upper- or lower-body garments or the wearable fitness technology thereof.

In one aspect, a system is provided for analyzing and managing the biometric or performance data collected. The system includes a graphical user interface or software application that is installed on a user's device and that enables the user the manage the data collected for tracking progress or planning future exercise schedules. Further, the system includes the ability to manage a plurality of users and/or a plurality of data sets authorized to a specific user.

In view of the foregoing, also provided herein in some embodiments is a resistance-training system including an upper-body garment having a first section of a single-layered construction and a second section of a multi-layered construction. The single-layered construction can include a first fabric layer. The multi-layered construction can include the first fabric layer, a second fabric layer, and a resistance-providing layer in-between the first fabric layer and the second fabric layer. The resistance-training system also includes a lower-body garment having the multi-layered construction, optionally with a different resistance-providing layer than the upper-body garment. The resistance-providing layer of the upper-body garment and the lower-body garment can be configured to provide resistance to one or more user movements for a user donning the resistance-training system. In some embodiments, the resistance-providing layer is anchored between opposing hems incorporating terminal ends of the first fabric layer, the second fabric layer, and the resistance-providing layer. In some embodiments, the opposing hems include collar and wrist hems of the upper-body garment. In some embodiments, the opposing hems include waist and ankle hems of the lower-body garment. In some embodiments, the resistance-providing layer is shorter in length between any two points on opposing hems than either the first fabric layer or the second fabric layer. In some embodiments, the resistance-providing layer is configured to freely stretch in-between the first fabric layer and the second fabric layer. In some embodiments, the upper-body garment includes a left-arm sleeve and a right-arm sleeve, and a glove or a hand loop is attached to each sleeve of the left-aim sleeve and the right-arm sleeve. In some embodiments, the lower-body garment includes a left pantleg and a right pantleg, and a stirrup is attached to each pantleg of the left pantleg and the right pantleg. In some embodiments, the lower-body garment includes the different resistance-providing layer than the upper-body garment, and the different resistance-providing layer has a larger modulus of elasticity than the resistance-providing layer of the upper-body garment. In some embodiments, the resistance-training system further includes one or more fitness-tracking devices removeably incorporated into one or both garments of the upper-body garment and the lower-body garment, wherein the one or more fitness-tracking devices are configured to collect fitness-related data selected from heart rate, steps taken, distance traveled, elevation, pace, calories burned, active minutes, and stationary time.

Also provided herein in some embodiments is a resistance-training system including an upper-body portion having a first section of a single-layered construction and a second section of a multi-layered construction. The single-layered construction can include a first fabric layer. The multi-layered construction can include the first fabric layer, a second fabric layer, and a resistance-providing layer in-between the first fabric layer and the second fabric layer. The resistance-providing layer can be an elastic fabric or an elastic sheet. The resistance-providing layer can be anchored between opposing hems incorporating terminal ends of the first fabric layer, the second fabric layer, and the resistance-providing layer. The resistance-providing layer can be shorter in length between any two points on the opposing hems than either the first fabric layer or the second fabric layer. The resistance-training system also includes a lower-body portion having the multi-layered construction, optionally with a different resistance-providing layer than the upper-body portion. The resistance-providing layer of the upper-body portion and the lower-body portion can be configured to provide resistance to one or more user movements for a user donning the resistance-training system. In some embodiments, the resistance-providing layer is an elastic sheet configured to freely stretch in-between the first fabric layer and the second fabric layer. In some embodiments, the lower-body portion includes the different resistance-providing layer than the upper-body portion, and the different resistance-providing layer has a larger modulus of elasticity than the resistance-providing layer of the upper-body portion. In some embodiments, the opposing hems include collar and wrist hems of the upper-body portion, the upper-body portion includes a left-arm sleeve and a right-aim sleeve, and a glove or a hand loop is attached to each sleeve of the left-arm sleeve and the right-arm sleeve. In some embodiments, the opposing hems include waist and ankle hems of the lower-body portion, the lower-body portion includes a left pantleg and a right pantleg, and a stirrup is attached to each pantleg of the left pantleg and the right pantleg. In some embodiments, the resistance-training system further includes one or more fitness-tracking devices removeably incorporated into one or both portions of the upper-body portion and the lower-body portion, wherein the one or more fitness-tracking devices are configured to collect fitness-related data selected from heart rate, steps taken, distance traveled, elevation, pace, calories burned, active minutes, and stationary time. In some embodiments, the resistance-training system is a two-garment resistance-training system, the upper-body portion is a first, upper-body garment of the two-garment resistance-training system, and the lower-body portion is a second, lower-body garment of the two-garment resistance-training system. In some embodiments, the resistance-training system is a single-garment resistance-training system, and the upper-body portion and the lower-body portion are two portions of the single garment.

Also provided herein in some embodiments is a resistance-training garment including an upper-body portion having a first section of a single-layered construction and a second section of a multi-layered construction. The single-layered construction can include a first fabric layer. The multi-layered construction can include the first fabric layer, a second fabric layer, and a resistance-providing layer in-between the first fabric layer and the second fabric layer. The resistance-providing layer can be anchored between opposing hems incorporating terminal ends of the first fabric layer, the second fabric layer, and the resistance-providing layer. The resistance-providing layer can be shorter in length between any two points on the opposing hems than either the first fabric layer or the second fabric layer. The resistance-providing layer can be configured to freely stretch in-between the first fabric layer and the second fabric layer. The resistance-training system also includes a lower-body portion having the multi-layered construction with a different resistance-providing layer than the upper-body portion. The different resistance-providing layer can have a larger modulus of elasticity than the resistance-providing layer of the upper-body portion. The resistance-providing layer of the upper-body portion and the lower-body portion can be configured to provide resistance to one or more user movements for a user donning the resistance-training garment. In some embodiments, the resistance-training garment further includes one or more fitness-tracking devices removeably incorporated into one or both portions of the upper-body portion and the lower-body portion, wherein the one or more fitness-tracking devices are configured to collect fitness-related data selected from heart rate, steps taken, distance traveled, elevation, pace, calories burned, active minutes, and stationary time.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A resistance-training system, comprising:
an upper-body garment comprising:
a first bottom section, a second top section, and a resistance-providing layer there-between;
the bottom section comprising a single-layered construction and a first fabric layer;
a top section comprising a multi-layered construction comprised of the first fabric layer and a second fabric layer, wherein the first fabric layer and second fabric layer have a first modulus of elasticity;
wherein the resistance-providing layer comprises:
i) an elastic material configured to expand or contract; and
ii) a second modulus of elasticity greater than the first modulus of elasticity of the first and second fabric layers to provide resistance;
wherein terminal ends of the first fabric layer, the second fabric layer, and the resistance-providing layer are anchored to one another in opposing hems including at a material transition line, thereby providing a proximity-based resistance with respect to a user's movement; and
a left-arm sleeve and a right-arm sleeve, wherein a glove or a hand loop is attached to each sleeve of the left-arm sleeve and the right-arm sleeve; the sleeves comprising a first length in a resting state, and a second length when stretched, the second length corresponding to the elasticity of the resistance-providing layer;
a lower-body garment having a multi-layered construction, comprising:
a waist band coupled to a first lower-body fabric layer;
a second lower-body fabric layer; and
a lower-body resistance-providing layer, wherein the modulus of elasticity of the lower-body resistance-providing layer is greater than the second modulus of elasticity; and
wherein the hem at the material transition line opposes a hem at the waist band.

2. The resistance-training system of claim 1,
wherein the opposing hems include collar and wrist hems of the upper-body garment.

3. The resistance-training system of claim 2,
wherein the opposing hems include waist and ankle hems of the lower-body garment.

4. The resistance-training system of claim 2,
wherein the resistance-providing layer is shorter in length between any two points on the opposing hems than either the first fabric layer or the second fabric layer, thereby increasing the basal resistance of the resistance-providing layer.

5. The resistance-training system of claim 2,
the resistance-providing layer is configured to freely stretch in-between the first fabric layer and the second fabric layer.

6. The resistance-training system of claim 2,
wherein the lower-body garment includes a left pantleg and a right pantleg, and
wherein a stirrup is attached to each pantleg of the left pantleg and the right pantleg.

7. The resistance-training system of claim 2, further comprising:
one or more fitness-tracking devices removably incorporated into one or both garments of the upper-body garment and the lower-body garment,
wherein the one or more fitness-tracking devices are configured to collect fitness-related data selected from heart rate, steps taken, distance traveled, elevation, pace, calories burned, active minutes, and stationary time.

8. A resistance-training system, comprising:
an upper-body portion comprising a multi-layered construction:
a first section configured as a single-layered construction comprising a first fabric layer; and
a second section configured as a multi-layered construction, wherein the multi-layered construction comprises the first fabric layer, and a second fabric layer, wherein the first fabric layer and second fabric layer have a first modulus of elasticity; and a resistance-providing layer comprising an elastic sheet in-between the first fabric layer and the second fabric layer, the elastic sheet comprising interlacing elastomeric material, wherein the resistance-providing layer comprises a second modulus of elasticity as compared to the first and second fabric layers, wherein the resistance-providing layer is configured as an elastic sheet to freely stretch in-between the first fabric layer and the second fabric layer, anchored between opposing hems incorporating terminal ends of the first fabric layer, the second fabric layer, and the resistance-providing layer, and is shorter in length between any two points on the opposing hems than either the first fabric layer or the second fabric layer, a lower-body portion comprising a multi-layered construction and a waist band coupled to a first lower-body fabric layer;

wherein a modulus of elasticity of a lower-body resistance-providing layer of the lower-body portion is greater than the second modulus of elasticity of the upper-body portion, thereby providing a proximity-based resistance with respect to a user's movement; and wherein terminal ends of the first fabric layer, the second fabric layer, and the resistance-providing layer are anchored to one another at a material transition line, and wherein a hem at the material transition line opposes a hem at the waist band; and wherein the upper-body portion includes a left-arm sleeve and a right-arm sleeves having a first length in a resting state, and a second length when stretched, the second length corresponding to the elastic sheet of the resistance-providing layer.

9. The resistance-training system of claim 8,
wherein the opposing hems include collar and wrist hems of the upper-body portion, and
wherein a glove or a hand loop is attached to each sleeve of the left-arm sleeve and the right-arm sleeve.

10. The resistance-training system of claim 8,
wherein the opposing hems include waist and ankle hems of the lower-body portion,
wherein the lower-body portion includes a left pantleg and a right pantleg, and
wherein a stirrup is attached to each pantleg of the left pantleg and the right pantleg.

11. The resistance-training system of claim 8, further comprising:
one or more fitness-tracking devices removably incorporated into one or both portions of the upper-body portion and the lower-body portion, wherein the one or more fitness-tracking devices are configured to collect fitness-related data selected from heart rate, steps taken, distance traveled, elevation, pace, calories burned, active minutes, and stationary time.

12. The resistance-training system of claim 8,
wherein the resistance-training system is a two-garment resistance-training system,
wherein the upper-body portion is a first, upper-body garment of the two-garment resistance-training system, and
wherein the lower-body portion is a second, lower-body garment of the two-garment resistance-training system.

13. The resistance-training system of claim 8,
wherein the resistance-training system is a single-garment resistance-training system, and
wherein the upper-body portion and the lower-body portion are two portions of the single garment.

14. The resistance-training garment of claim 8, further comprising:
one or more fitness-tracking devices removably incorporated into one or both portions of the upper-body portion and the lower-body portion,
wherein the one or more fitness-tracking devices are configured to collect fitness-related data selected from heart rate, steps taken, distance traveled, elevation, pace, calories burned, active minutes, and stationary time.

* * * * *